(12) United States Patent
Deur

(10) Patent No.: US 11,000,674 B2
(45) Date of Patent: May 11, 2021

(54) LOW PROFILE LUMEN ACCESS CATHETER

(71) Applicant: Advanced Vascular Access Systems, LLC, Hollidaysburg, PA (US)

(72) Inventor: Tomislav Deur, Hollidaysburg, PA (US)

(*) Notice: Subject to any disclaimer, the term of this patent is extended or adjusted under 35 U.S.C. 154(b) by 718 days.

(21) Appl. No.: 15/462,892

(22) Filed: Mar. 19, 2017

(65) Prior Publication Data
US 2018/0264233 A1    Sep. 20, 2018

(51) Int. Cl.
*A61M 25/04* (2006.01)
*A61M 25/00* (2006.01)
*A61M 25/01* (2006.01)
A61M 25/02 (2006.01)

(52) U.S. Cl.
CPC .......... *A61M 25/04* (2013.01); *A61M 25/003* (2013.01); *A61M 25/0074* (2013.01); *A61M 25/0108* (2013.01); A61M 2025/0079 (2013.01); A61M 2025/028 (2013.01); A61M 2205/0266 (2013.01); A61M 2205/058 (2013.01); A61M 2210/1085 (2013.01)

(58) Field of Classification Search
CPC ........ A61M 2025/0687; A61M 25/003; A61M 25/0074; A61M 2025/0079; A61M 25/04; A61M 25/0108; A61M 2025/028
See application file for complete search history.

(56) References Cited

U.S. PATENT DOCUMENTS

2002/0173817 A1\* 11/2002 Kletschka ........ A61B 17/22032
606/194
2005/0187578 A1\* 8/2005 Rosenberg ............ A61M 25/04
606/232

\* cited by examiner

*Primary Examiner* — Jason E Flick
*Assistant Examiner* — Tasnim Mehjabin Ahmed

(57) ABSTRACT

A temporary low profile intraluminal catheter for infusing agents into, or extracting fluids from, a bodily lumen featuring securement structure, wherein the securement structure allows the catheter to be placed with minimal intrusion into the bodily lumen is disclosed. With such design affording a more efficient, verifiable placement of the catheter with less complication due to infection and biofilm related issues, among other types of complications.

2 Claims, 3 Drawing Sheets

LOW PROFILE LUMEN ACCESS CATHETER

BACKGROUND

The central venous catheter is a medical device which can allow blood sampling, blood pressure monitoring, and the administration of fluid, blood and medication to a patient. A central venous catheter is percutaneously inserted, via the Seldinger technique, such that the distal catheter tip resides within a large caliber vein, and the proximal portion of the catheter lies external to the patient's body. Typically, a central venous catheter is inserted into an internal jugular vein or subclavian vein with its distal tip residing within the superior vena cava. After the placement of a central venous, a chest x-ray is obtained to identify that the distal tip of the catheter is appropriately positioned in the region of the superior vena cava prior to being used. The central venous catheter is commonly used, particularly in hospital intensive care units, due to the need for reliable venous access in the medical management of acutely ill patients.

The central venous catheter has become a staple item in helping medical personnel care for patients, but it is also associated with numerous immediate and delayed complications. Immediate complications can arise at the time of the catheter's insertion and can include, but are not limited to, hematomas or bleeding, inadvertent cannulation of an artery, pneumothorax or cardiac arrhythmias. With appropriate technique and ultrasound guidance many of the immediate complications can be avoided. The delayed complications associated with central venous catheters can present significant obstacles in managing a patient's healthcare.

When a central venous catheter is inserted into the lumen of a vein, proteins begin to deposit along the surface of the catheter creating a catheter related sheath (CRS). These sheaths can be asymptomatic, but can also result in numerous delayed complications:

When the CRS covers the catheter's opening, it can effectively occlude the central venous catheter.

If the CRS wraps around the entire length of the indwelling central venous catheter it can result in medical extravasation into the adjacent soft tissues as the medication tracks retrograde in between the catheter opening and sheath to the entry site of the catheter into the vein.

The CRS enhances central venous catheter infections and persistent bacteremia.

The CRS can lead to a stenosis or occlusion of the vein in which the catheter resides. A central venous stenosis poses significant problem to patients, particularly chronic end-stage renal dialysis patients with upper extremity arterial venous fistulas or grafts, who need adequate venous outflow to maintain patency of their fistulas or grafts.

A significant length of the central venous catheter lies within the lumen of a vein which provides a large surface area for CRS development and its subsequent complications. The distal tip of a central venous catheter is mobile within the lumen of a vein and constantly moves due to blood flow, respiration and cardiac motion. This constant motion results in repeated micro-trauma to the adjacent vein wall, which can result in thrombus formation along the catheter tip or adjacent vein wall. This thrombus can result in catheter malfunction, by obstructing the catheter lumen, or stenosis of the vein lumen.

The complications associated with central venous catheters pose significant issues with regards to managing the healthcare of acutely ill patients. The proposed catheter aims to diminish the myriad complications associated with current central venous catheters.

SUMMARY

The present invention provides many advantages when compared with existing techniques and devices; these advantages include, but are not limited to:

The catheter is designed to be inserted under ultrasound guidance in the attempt to minimize immediate complications.

When appropriately positioned, only the distal tip of the central venous catheter protrudes into the vein. The design attempts to maintain robust venous blood flow through the cannulated vein in the attempt to prevent venous stasis, subsequent thrombosis and possible venous stenosis.

The positioning of the distal catheter tip is verified using ultrasound. Therefore, the need for a subsequent chest x-ray to evaluate the positioning of the catheter is eliminated.

Since only the distal tip of the catheter protrudes into the lumen of the vein, the overall catheter surface area exposed to the development of CRS is significantly reduced relative to existing central venous catheters. This has the potential to significantly reduce the chances of a catheter infection and bacteremia. The reduced CRS also has the potential to reduce the opportunity of venous stenosis and occlusions.

No portion of the catheter is permitted to freely move within the vessel lumen. This eliminates the repeated micro-trauma to the vein wall and subsequent thrombus formation associated with freely mobile catheter tips.

The catheter opening(s), along the distal tip of the catheter, are designed to be mechanically opened and closed which prevents blood from clotting within the lumen of the catheter and provides a mechanical mechanism to disrupt fibrin or thrombus accumulation at the distal tip of the catheter. The preferred embodiment contains two openings, but certain procedures may benefit from a single opening, while greater than two openings may benefit fluid flow as well.

A proposed mechanism used to open the catheter to blood flow creates a covering over the catheter's distal tip openings. This would prevent a vein wall from potentially obstructing the catheter opening when a negative pressure is exerted through the central venous catheter, as in the example of a blood draw through the catheter.

The proposed catheter design can meet an existing need by providing a reliable, secure method of obtaining short term venous access while diminishing complications associated with existing central venous catheter designs. While significant description refers to venous lumens, it is recognized that arterial lumens may also be treated with the present device.

In a preferred embodiment, this disclosure describes a temporary intraluminal catheter for infusing agents into a bodily lumen. The catheter includes a proximal end, a distal end, and a mid-section; with a main lumen running along the length of the catheter. The main lumen defines a main axis, and the main lumen terminates at a distal lumen orifice. The distal lumen orifice is designed to provide liquid communication from the main device lumen into a bodily lumen. While the term "bodily lumen" is used, it is recognized that this device could be used effectively in a bodily organ or tissue having an opening or open space, whether man-made or natural. The most common uses for the present device may be in accessing the internal jugular vein or femoral vein.

This preferred embodiment also includes a securement means located at the aforementioned distal end, wherein said securement means comprises two diametrically opposed shape memory material anchors. At least two securement channels, wherein said securement channels comprise passageways for the reversible proximal to distal travel of said securement means, and wherein said securement channels traverse at least a portion of the catheter's mid-section along its main axis and ultimately exit the distal end in a direction approximately tangential to the main axis of said catheter body. It is recognized that the angle of the end of the device (or the angle of the distal lumen orifice) can affect the flow of fluid from the device, as well as the flow of fluid in the lumen. This effect may be useful in various ways; traditionally, avoiding turbulent blood flow is very beneficial to prevent clotting (because turbulent flow, among other things, causes areas of high flow along with areas of low flow, and areas of low flow are prone to clotting), but in certain instances turbulence causes better mixing action which may be useful for introducing compounds less soluble in bodily fluids (e.g., cisplatin in blood). The turbulent effects may be more pronounced when the pharmaceuticals or compounds are introduced in a bolus format.

Embodiments containing two securement means, or a securement means design which has such means in opposing directions, may result in a system that automatically aligns itself with regard to the bodily lumen. Those skilled in the art should understand that certain placement of securement means would cause the device to tend to seat itself in a certain orientation. Additionally, the device, toward the proximal end, may have directional indicators such that the person implanting the device will know the orientation of the distal end.

In this preferred embodiment, the securement means are located near the tip of the device, and such placement causes a minimal length of catheter device being disposed in the bodily lumen. Reducing the amount of foreign body in the lumen reduces the incidence of CRS and infection due to fibrin film build-up.

A preferred embodiment also includes actuators to operate the securement means, an optimum design would likely include two actuators arranged to operate each of two securement means. The actuation of the actuator in a distal manner would cause the securement means to exit the securement channel and to be exposed inside the bodily lumen.

In a preferred embodiment, the shape memory character allows the securement means to align the distal end of the device with the lumen. Additionally, the securement means may provide positive feedback of location within said bodily lumen, to assist with placement of the device.

A preferred embodiment may also contain more than one lumen. In this type of design, at least a second lumen has a corresponding second orifice for egress or ingress of fluid. In this regard, it is recognized that a single securement means may be beneficial (e.g., in very small catheters, intended for very small lumens in the vascular anatomy, or where the device itself has more than one lumen and not room for more than one securement means) but several securement means may also serve to better anchor or better position the device.

A preferred embodiment may include a lumen closing means, where such means is a plugging type mechanism or a member capable of rotational movement to block the distal lumen orifice(s). This could be designed in devices with a singular or a plurality of lumens. It is recognized that one skilled in the art will easily envision alternate lumen closing means, which will serve to block fluid flow through such lumens; the examples provided herein are not meant to be exhaustive. While blocking fluid flow, the lumen closing means may also serve to avoid trapping, snaring, or snagging tissue during implantation or movement of the device.

Embodiments containing lumen closing means may contain lumen closing actuators and the actuators may be located in closing actuator channels. The actuators will be designed to be operated from the proximal end of the device.

Devices containing a plurality of either lumen closing means or securement means, or both, may have actuators that operate all of such closing means concurrently or all of such securement means concurrently. Alternatively, each of such means may be operated independently of the remaining same type of means.

A preferred embodiment has a distal end, with at least one distal lumen orifice, that is shaped to minimize flow disruption. This shape may in certain instances be referred to as a "low profile," and it may be generally designed with a contour to minimize disruption of flow and further minimizing turbulent flow.

Another preferred embodiment includes a securement means that has tissue protection means. The securement means may scrape or otherwise impinge on the inner lumen tissue during deployment of the securement means. Depending on the mechanics of deployment, the tissue type, or the anatomy, at the site, the deployment may cause tissue damage. Tissue protection means may minimize or eliminate such damage, and said means may be in the form of a telescoping member at the end of the securement means or a rolling member arranged to roll along or over the tissue (e.g., similar to a baker's rolling pin) during deployment. It is recognized that other protection means may be substituted for these examples, and some may be very rudimentary; for example, the protection may be afforded the device by the shape of the end of the securement means.

In yet another preferred embodiment, a temporary intraluminal catheter for infusing or extracting fluid into or from a lumen or bodily cavity is arranged to additionally provide locating means and steering means.

The locating means consists of providing a radiopaque component arranged at or near the distal tip of the catheter; additionally, the locating means may be arranged at the tips of said securement means, or a combination of the foregoing. Locating means may serve dual functions, in that they may allow a physician to confirm the placement of the device, especially when the device is used internally at a deep location in the body; or the locating means may be used to affirm that securement means is being deployed in a particular direction or to a particular point. In this fashion, the locating means may aid a steering means.

The steering means may be integral to the embodiments with a plurality of securement means, wherein the securement means operates to press on a lumen or other bodily tissue to reposition or steer the tip of the catheter. For example, independent operation of primary securement means may also provide feedback to the user, with such independent operation allowing the preferential positioning of the distal end within a lumen or body cavity. Furthermore, this selective positioning enables further advancement in a desired direction. However, operating in this manner, the securement means may serve to stabilize the distal end from movement caused by pulsing or uneven flow or bodily fluid in said lumen or body cavity.

Steering means may also benefit from securement means arranged at uneven points around the circumference of the distal end, with such primary securement means being more densely located on a dominant side. Dense placement may allow uneven pressure to be more effectively exerted, enabling the device to be shifted or directed. Directional indicators may be beneficial for steering procedures, so initial direction may be set external to the patient.

These embodiments may also comprise an auxiliary channel arranged to accept a guidewire or other diagnostic device. In certain embodiments, the main lumen could be arranged to serve as an auxiliary channel.

DETAILED DESCRIPTION

Figure 1:
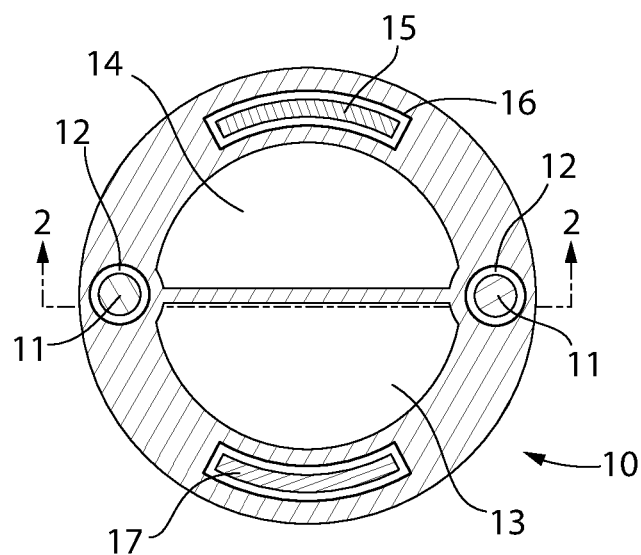
FIG. 1 is an elevational view of a preferred embodiment of the present invention, showing a lumen cross section.

Reference is made to FIG. 1 for the illustration of one preferred embodiment of a temporary intraluminal catheter for infusing or extracting fluid into or from a lumen or bodily cavity constructed according to the present invention which includes a main catheter body, designated generally by the reference numeral 10. The main catheter body 10 houses various components of the device, for example, securement means 11 are arranged within securement means channels 12. A single securement means may be employed (not shown) but preferred embodiments generally employ two securement means (as shown); however, additional securement means may be used (not shown) and the design may include offset placement, to provide directional pressure upon their interaction with bodily tissue.

This preferred embodiment also utilizes a main or primary lumen 13, terminating at a distal lumen orifice (not shown), and a second or secondary lumen 14. These lumens may be opened or closed by the distal-to-proximal movement of distal lumen orifice closures 15, which arranged to move along an orifice closure channel 16. It is contemplated that each lumen will be arranged with a distal lumen orifice closure; however, one closure may be left off such that a guide wire may be used to initially place the device within the body, or so a diagnostic device may be introduced through the lumen. Alternatively, the lumen 13 and the distal lumen orifice closure 15 may be sized such that said guidewire or diagnostic device may exit the orifice itself with the closure in its most distal location (not shown).

Figure 2:
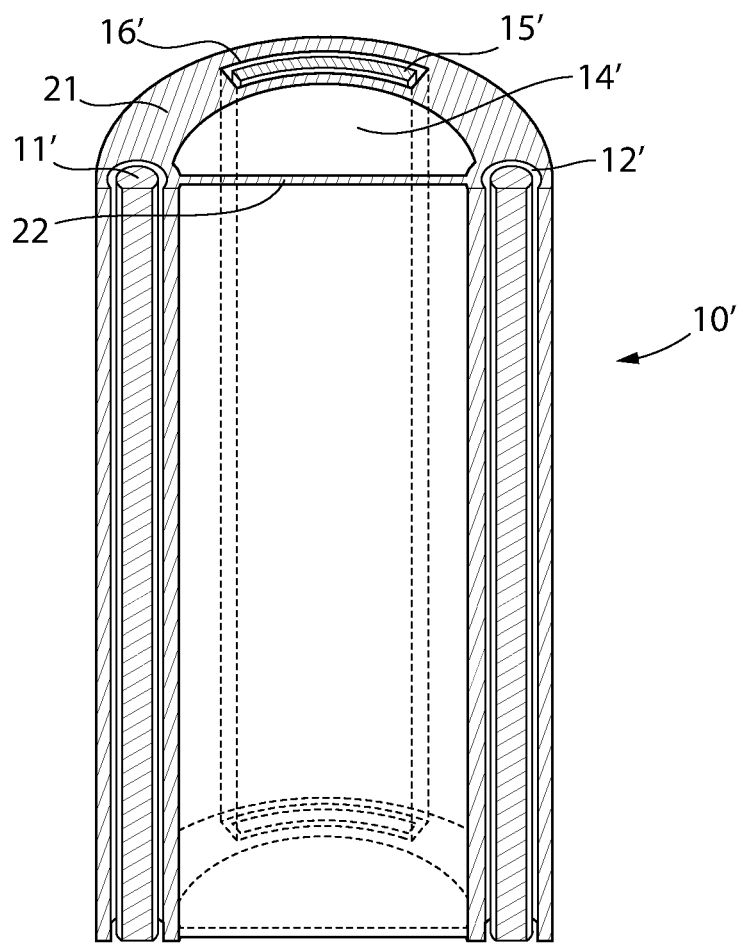
FIG. 2 is an elevational view of a preferred embodiment of the present invention, showing a cut away section view through the section 2-2 indicated in FIG. 1.

Reference is now made to another preferred embodiment of the present invention, which is illustrated at FIG. 2. The same structures, components and features existing in this embodiment; that have been introduced in previous figure(s) or embodiments will be represented by the same reference numeral with, however, the addition of a prime marking. In instances where this scheme may cause confusion, for example, a component in a similar location, but serving a different function, such component may be assigned a new numeric designation. This sectional elevational view shows the main catheter body 10' with the secondary lumen 14' running axially along the length of the main catheter body 10,' the proximal end and the distal ends of the device are not shown.

The main catheter wall 21 may comprise a diametric central member 22 arranged to segregate the secondary lumen 14' from the primary lumen 13 (not shown in this view).

Figure 3:
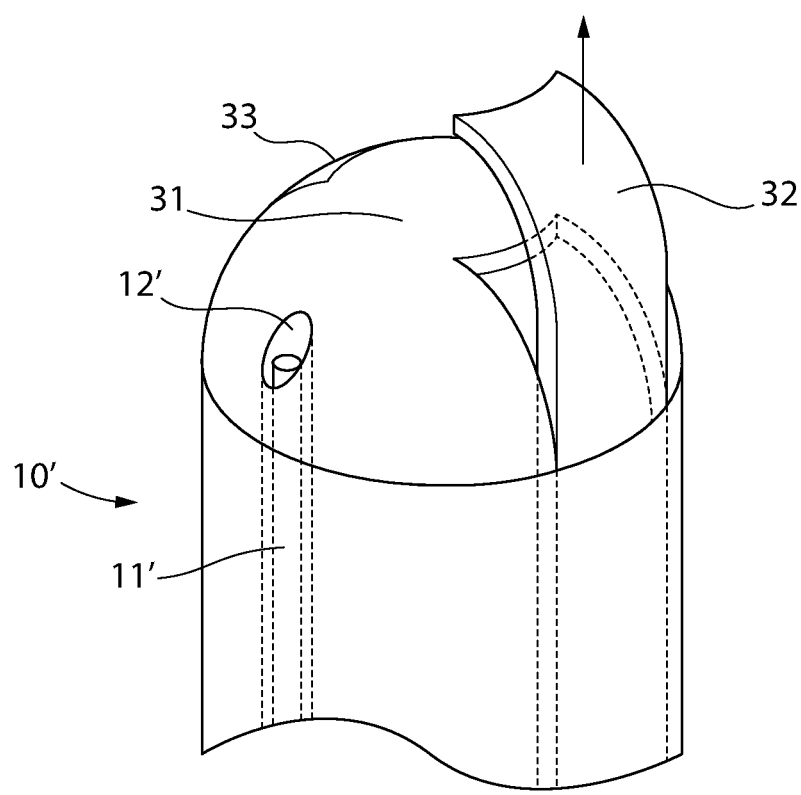
FIG. 3 is a perspective view of a preferred embodiment showing an isometric view.

Reference is now made to the perspective view at FIG. 3, showing a main catheter body 10' of a preferred embodiment. This embodiment highlights the distal tip 31 of the device, and the embodiment comprises a dual lumen design with an arcuate shaped primary lumen orifice closure tip 32 and an arcuate shaped secondary lumen orifice closure tip 33. The secondary lumen orifice closure 33 is in its proximal position thereby closing flow into the secondary lumen (not shown), this proximal positioning may be altered by movement of the lumen orifice closure 15 (not shown, but see FIGS. 1 and 2). The primary lumen orifice closure tip 32 is in its distal position, as shown by the arrow. This positioning may be altered by movement of the primary lumen orifice closure 17 (not shown, but see FIG. 1); but in this position the lumen is open to the flow of fluid.

This particular view also shows the securement means 11' in its proximal non-deployed orientation inside the securement means channel 12'. This view shows a single securement means 11,' but a plurality may be used as has been described in previous embodiments and configurations.

Figure 4:
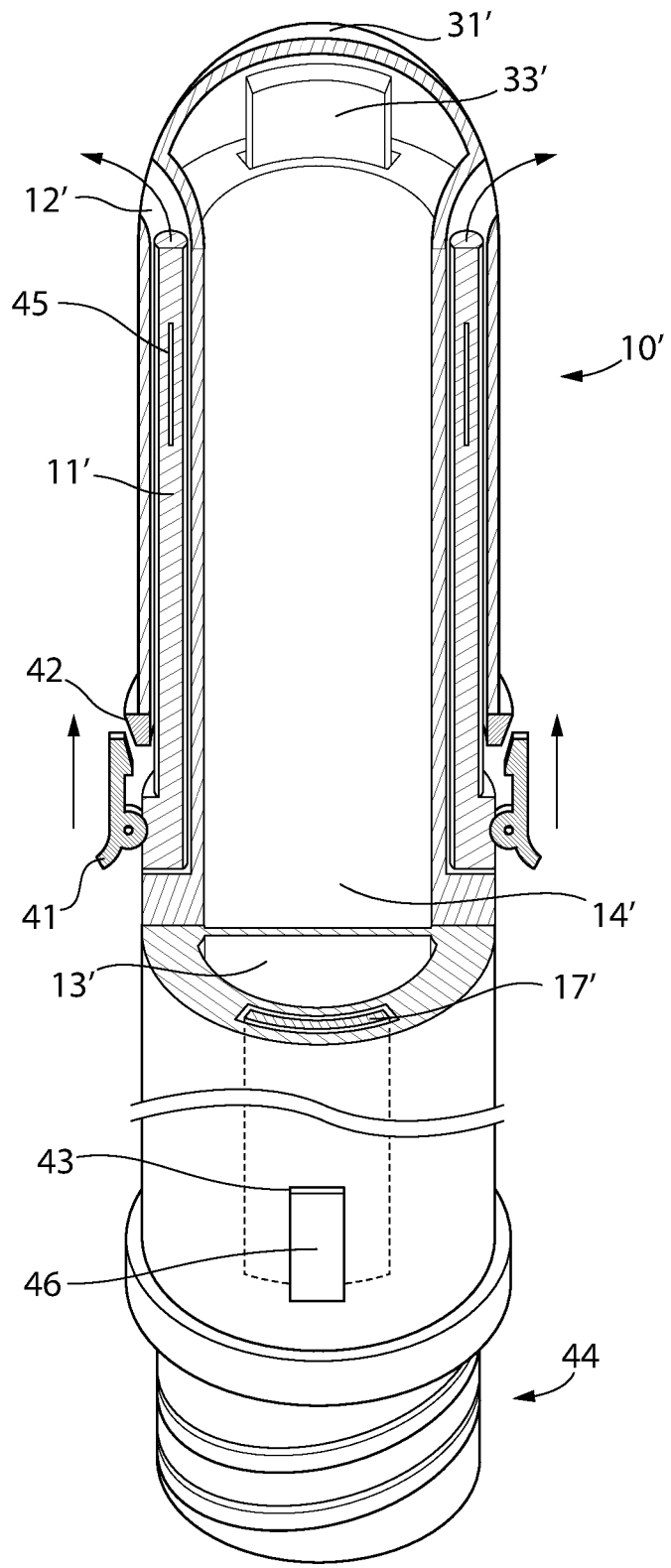
FIG. 4 is a view showing a partial cut-away view of a preferred embodiment of the device assembly.

Reference is now made to another preferred embodiment of the present invention, which is illustrated at FIG. 4; an elevational view showing a partial cut-away region. This drawing represents various embodiments of the main catheter body 10', in a manner to better show the function of the securement means 11' and a primary lumen orifice closure 17' as well as the lumen orifice closure tip 33,' as operated by a secondary lumen orifice closure 15' (not shown). This drawing represents a dual lumen, dual securement means design; however, additional lumens and or additional securement means may be added. Those skilled in the art can appreciate the geometric changes necessary to accommodate additional numbers of features such as these; there are limitations based on the overall size of the catheter. The catheter sizing may be different for various parts of the anatomy.

The present invention is contemplated for use within the arterial or venous vasculature; however, use in other bodily lumens and pathways will benefit from the advantages inherent in this device. For example, a person may have a percutaneous nephrostomy in which a catheter is inserted through the skin, kidney parenchyma and then into the renal pelvis then ureter. The catheter is then pushed further down the ureter (to bypass, for example, an obstructing calculus, stricture, or tumor) so that its distal end resides in the bladder lumen. The distal tip 31' of that catheter can then be "anchored" in place with the securement means 11' of the instant invention to prevent it from sliding out of it place.

This illustration shows, among other things, the manner in which the securement means 11' operates. A securement latch 41 may employed to hold the securement means 11' stationary in the distal or deployed position. Deployment may be accomplished by pushing the securement latch 41 from its proximal position (shown) in the direction of the arrow, to its distal location, whereupon the securement latch 41 will releasably engage with locking tab 42. This will allow the catheter device 10' to rest, or remain in a fixed, deployed state, while serving to, among other things, infuse or evacuate fluids.

Fluids may be directed, at least in part, by the orientation of the device, while in the lumen. If a fluid, blood for example, is flowing in a vein, and the secondary lumen orifice closure tip 33' were deployed to its distal position, it would capture blood and direct it along the arcuate inner surface (in this example, assume the blood is flowing in the direction from front to back, or into the paper), and along the secondary lumen orifice closure 15 (not shown) and into the secondary lumen 14'. Similarly, fluid could be introduced into the body, in the direction of this flow, thereby reducing turbulence. To achieve this result, the primary lumen orifice tip 32 (not shown) may be deployed; the arcuate shape of the outer surface would serve to deflect or reroute blood in a more laminar and non-turbulent fashion, while the infusate travels through the primary lumen 13' in a distal direction, until it is redirected by the inner arcuate surface of the primary lumen orifice tip 32 (not shown).

Deployment of the primary lumen orifice tip 32 (not shown) may be accomplished by pushing the primary orifice latch 43 into its distal position in the latch's slot 46 (as shown) from its proximal position in the latch's slot 46 (not shown), whereupon the primary lumen orifice tip 32 (not shown) will be deployed (as was shown at FIG. 3). Deployment of the secondary lumen orifice tip 33' (or any additional such orifice openings) may be deployed in similar fashion, with their corresponding latches (not shown).

These various embodiments may benefit from a coupling 44 arranged to accept standard medical equipment (e.g., threaded, barbed or Luer types of fittings) to enable the infusion or capture of fluids, or to enable the introduction of a diagnostic device. Additionally, a plurality of couplings (not shown) may be used to separate fluid flow through the various device lumens, or a single coupling with a plurality of fluid pathways (not shown) may achieve the same purpose.

These various embodiments may also benefit from a radiopaque marker 45 placed on the securement means 11', which will serve to assist the location of the securement means 11'. This may be especially important when the distal end of the catheter body 11' is further internal to the anatomy such that ultrasound locating is not an option. Additionally, a radiopaque marker, member, or coating (as is known to those skilled in the art), may be incorporated in the design near the tip 31 (not shown).

The embodiments herein utilizing a securement latch 41, arranged to releasably couple with locking tab 42, or the like, may also comprise a securement latch arranged to act in the opposing (i.e., proximal) direction and an associated locking tab (not shown). This arrangement would allow the locking of the securement means in the proximal (i.e., stowed) position.

The securement means 11' may comprise shape memory materials. Various forms of these engineering materials are known to those skilled in the art; but, among other things, they generally have one of two features that render them valuable to certain mechanical designs. These materials either undergo a diffusionless transformation at a set temperature, or they experience superelasticity and retain a set shape. Both types of materials are contemplated by this disclosure; but the composition or treatment (whether polymeric, metallic, compound, or composites thereof) is not a claimed aspect of the present invention, and is therefore not specifically described in detail.

By way of example, the securement means 11' may be made of a superelastic material, that undergoes high strain in an elastic manner, and returns to its original shape upon the release of the induced stress (i.e., returns to its original shape). Utilizing this material property, a securement means 11' may be constructed of a superelastic shape memory alloy, wherein the securement means 11' experiences heavy strain as it translates in a proximal direction (as shown by the arrow in FIG. 4) outward through securement means channel 12'. The securement means 11' would return to a straight geometry follow the exit from the securement means channel 12'. In this embodiment, the securement means 11' construction as well as the shape or geometry of the securement means channel 12' play a role in dictating the direction of the securement means 11' deployment.

A superelastic material could be fabricated with a "bend" (e.g., at 90 degrees) or other configuration set by fabrication method or heat treatment (not shown). This material could be strained to a straight dimension, and then return to the preset shape following the release of the induced stress/strain. In this manner, a securement means 11' may be fabricated, and stowed in the securement means channel 12'. Turning now to FIG. 3, a securement means channel may exit the distal tip 31 in a direction more in-line or coaxial with the catheter's longitudinal axis. The securement means 11' would be in a stressed state while stowed within the securement means channel 12;' and upon deployment (which may be achieved, for example, by means such as those in the discussion in the text regarding FIG. 4) the stresses would be released and the securement means 11' would return to its preset (e.g., bent) shape.

Alternatively, a shape memory alloy which exhibits a phase change upon exposure to a set temperature may be used to construct the securement means 11'. Optimally, the transition inducing temperature would be just below body temperature; and as the securement means 11' were deployed from the securement means channel 12' it would experience a rise in temperature and undergo a phase transformation which would cause it to return to a preset shape.

In either of these shape memory alloy material embodiments the preset shape (not shown) could be a 90 degree bend, an arcuate section arranged to put slight back pressure on the lumen wall, or other shape designed to cause the distal tip 31 to rest at an optimal location within the bodily lumen of cavity.

While this disclosure refers to general illustrative embodiments as well as various particular embodiments, it should be understood that the disclosure is not limited thereto. Modifications can be made to the embodiments described herein without departing from the spirit and scope of the present disclosure, even where certain modifications are suggested, the list or set of proposed modifications is not necessarily exhaustive. Those skilled in the art with access to this disclosure will recognize additional modifications, embodiments, and methods of use within the scope of this disclosure; and similarly, additional fields of use in which the disclosed invention could be applied are contemplated. Therefore, this detailed description is meant to be enabling but not meant to be limiting. Further, it is understood that the apparatus and methods described herein can be implemented in many different embodiments of hardware, devices, or systems. Any actual apparatus, method of manufacture, or method of use, described is likewise not meant to be limiting. The operation and behavior of the apparatus and methods presented are described with the understanding that modifications and variations of the embodiments as well as modalities of use and operation are possible; with each modification potentially influencing the operation or outcome.

What is claimed is:

1. A temporary intraluminal catheter for infusing or extracting fluid into or from a bodily lumen, comprising:
- a catheter body comprising a proximal end, a distal end, and a mid-section;
- a main lumen running along a length of said catheter, thereby defining a main axis, and terminating at a distal lumen orifice, wherein said distal lumen orifice is arranged to provide liquid communication from said main lumen to the bodily lumen with said liquid communication being regulated by a distal lumen orifice closure;
- at least a first securement means located at said distal end, wherein said first securement means comprises a shape memory material anchor, and is arranged to provide positive feedback of location within the bodily lumen;
- at least a first securement channel, wherein said first securement channel comprises a passageway for a proximal-to-distal and distal-to-proximal travel of said securement means, and wherein said securement channel traverses at least a portion of said catheter mid-section along its main axis and ultimately exits said distal end in a direction approximately tangential to the main axis of said catheter body;
- at least a first securement means actuator, wherein distal actuation of said actuator causes said securement means to exit said securement channel and to be disposed internal to the bodily lumen; and
- at least a second securement means arranged to be operated by a second securement means actuator disposed in a second securement channel.

2. The catheter of claim 1, wherein said first securement means is arranged to be operated independently of said second securement means.

* * * * *